US006842235B2

(12) United States Patent
Zaidi et al.

(10) Patent No.: US 6,842,235 B2
(45) Date of Patent: Jan. 11, 2005

(54) OPTICAL MEASUREMENT OF PLANARIZED FEATURES

(75) Inventors: Syed Shoaib Hasan Zaidi, Poughkeepsie, NY (US); Gangadhara S. Mathad, Poughkeepsie, NY (US)

(73) Assignee: Infineon Technologies North America Corp., Cary, NC (US)

( * ) Notice: Subject to any disclaimer, the term of this patent is extended or adjusted under 35 U.S.C. 154(b) by 224 days.

(21) Appl. No.: 09/966,506

(22) Filed: Sep. 28, 2001

(65) Prior Publication Data

US 2003/0063272 A1 Apr. 3, 2003

(51) Int. Cl.[7] .............................................. G01N 21/00
(52) U.S. Cl. ...................................... 356/72; 356/237.2
(58) Field of Search .......................... 356/237.1–237.5, 356/72

(56) References Cited

U.S. PATENT DOCUMENTS 5,432,607 A * 7/1995 Taubenblatt ................. 356/364
6,307,627 B1 * 10/2001 Vurens ........................ 356/369
6,437,862 B1 * 8/2002 Miyazaki et al. ......... 356/237.2
6,538,731 B2 * 3/2003 Niu et al. ................. 356/237.5
6,545,753 B2 * 4/2003 Subramanian et al. ... 356/237.5
6,570,662 B1 * 5/2003 Schictinger et al. ........ 356/630

* cited by examiner

Primary Examiner—Michael P. Stafira
(74) Attorney, Agent, or Firm—Edell, Shapiro & Finnan LLC

(57) ABSTRACT

There is provided a method for measuring planarized features on a wafer of a semiconductor device. The planarized features on the wafer are illuminated. A reflected light beam with respect to the planarized features is detected. Optical characteristics of the reflected light beam are analyzed to determine information corresponding to the planarized features. Preferably, the analyzing step maximizes an analysis of the optical characteristics based upon a simplified geometry of the planarized features with respect to a geometry of similar, un-planarized features. Moreover, preferably, the analyzing step maximizes an analysis of the optical characteristics based upon a reduction in complexity of the planarized features due to a similarity in refractive indexes corresponding to a bulk silicon substrate and a poly silicon fill of the semiconductor device.

19 Claims, 4 Drawing Sheets

OPTICAL MEASUREMENT OF PLANARIZED FEATURES

BACKGROUND

1. Technical Field

The present invention generally relates to semiconductor fabrication and, in particular, to a system and method for optical measurement of planarized features.

2. Background Description

Process control is becoming very critical with escalating processing costs and large wafer size. Out-of-specification processes result in large yield losses and thereby affect fabrication productivity. Real-time measurements of key process parameters (e.g., etch rates) are sometimes very difficult due to nanometer scale dimensions or a lack of non-perturbing measurement techniques.

However, it is often possible to correlate incoming feature dimensions to process and, in such a case, correlations can be developed between in-situ measurements (e.g., trench opening) of every processed wafer and a process parameter like etch rate. These correlations, in turn, can be uses to predict process end points and thereby control processes. Currently available optical methods provide only off-time measurement capabilities for monitoring purposes and hence are unsuited for real-time control.

The problem solved by the present invention is different from a large body of work presented by Raymond et al. in the following: C. J. Raymond, in "Milestones and Future Directions in Applications of Optical Scatterometry", Optical Metrology, Proc. SPIE CR72, pp. 147–177, 1999; C. J. Raymond, in "In-situ Metrology", Handbook of Semiconductor Manufacturing Technology, edited by Nishi et al., published by Marcell Dekker, 2000; C. J. Raymond, in "Scatterometry for Semiconductor Metrology", Handbook of Silicon Semiconductor Metrology, edited by A. Diebold, to be published by Marcell Dekker, 2001; Raymond et al., in "Resist and Etched Line Profile Characterization Using Scatterometry", Integrated Circuit Metrology, Inspection and Process Control XI, Proc. SPIE 3050, 1997; Raymond et al., in "Metrology of Subwavelength Photoresist Gratings Using Optical Scatterometry", Journal of Vacuum Science and Technology B, 13(4), pp. 1484–1495, 1995; Raymond et al., in "Multi-Parameter Grating Metrology Using Optical Scatterometry", Journal of Vacuum Science and Technology B, B15(2), 1997. Raymond's work describes gratings with surface profiles. The features in the inventions described by Raymond have not been planarized and consequently have significant surface reliefs.

The problem solved by the present invention is also different from that described by Milner et al., in "Latent Image Exposure Monitor Using Scatterometry", SPIE Vol. 1673, pp. 274–283, 1992. The preceding is directed to latent images in photoresists. These gratings do not have surface relief but are planar gratings. Primarily, the features mentioned in Milner's work are latent images in photo resist. The difference in the refractive indices in the constituent components of these phase gratings is very small. In addition, the difference in the refractive indices is limited to the resist layer as the underlying anti-reflection coatings are not affected by exposure to light.

SUMMARY OF THE INVENTION

The problems stated above, as well as other related problems of the prior art, are solved by the present invention, a system and method for optical measurement of planarized features.

Dimensions of features determine the operating characteristics of semiconductor devices. The measurements of these features are difficult due to their small size. The present invention provides a non-contact, non-destructive technique for measuring the critical dimensions of poly-filled DRAM trenches and similar structures based on optical measurements.

One common problem with the analysis of signals from periodic structures (in scatterometry, ellipsometry, polarimetry, and so forth) is extracting useful information from the complex spectra collected in measurements. The key feature of the present invention is simplification of the analysis of signals from periodic signals by exploiting (1) simplified geometry due to planarization (which results in features that do not have significant surface reliefs) and (2) reduction in complexity of the features due to the similarity in the refractive index of the bulk silicon and the poly silicon fill. These simplifications provide means to effective implementation of optical techniques for measuring the critical dimensions of the features.

According to an aspect of the present invention, there is provided a method for measuring planarized features on a wafer of a semiconductor device. The planarized features on the wafer are illuminated. A reflected light beam with respect to the planarized features is detected. Optical characteristics of the reflected light beam are analyzed to determine information corresponding to the planarized features.

According to another aspect of the present invention, the information comprises sizes of the planarized features.

According to yet another aspect of the present invention, the information comprises grating compositions of the planarized features.

According to still yet another aspect of the present invention, the detection tool employs at least one of an ellipsometric, a scatterometric, a reflectometric, and a polarimetric technique to detect the reflected light.

According to a further aspect of the present invention, the analyzing step maximizes an analysis of the optical characteristics based upon a simplified geometry of the planarized features with respect to a geometry of similar, un-planarized features.

According to a still further aspect of the present invention, the analyzing step maximizes an analysis of the optical characteristics based upon a reduction in complexity of the planarized features due to a similarity in refractive indexes corresponding to a bulk silicon substrate and a poly silicon fill of the semiconductor device.

According to an additional aspect of the present invention, there is provided a system for measuring planarized features on a wafer of a semiconductor device. An illumination tool illuminates the planarized features on the wafer. A detection tool detects a reflected light beam with respect to the planarized features. An analysis tool analyzes optical characteristics of the reflected light beam to determine information corresponding to the planarized features.

These and other aspects, features and advantages of the present invention will become apparent from the following detailed description of preferred embodiments, which is to be read in connection with the accompanying drawings.

DETAILED DESCRIPTION OF PREFERRED EMBODIMENTS

The present invention is directed to a system and method for optical measurement of planarized features.

It is to be understood that the present invention may be implemented in various forms of hardware, software, firmware, special purpose processors, or a combination thereof. Preferably, the present invention is implemented as a combination of hardware and software. Moreover, the software is preferably implemented as an application program tangibly embodied on a program storage device. The application program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) that is executed via the operating system. In addition, various other peripheral devices may be connected to the computer platform such as an additional data storage device and a printing device.

It is to be further understood that, because some of the constituent system components and method steps depicted in the accompanying Figures are preferably implemented in software, the actual connections between the system components (or the process steps) may differ depending upon the manner in which the present invention is programmed. Given the teachings herein, one of ordinary skill in the related art will be able to contemplate these and similar implementations or configurations of the present invention.

Figure 1:
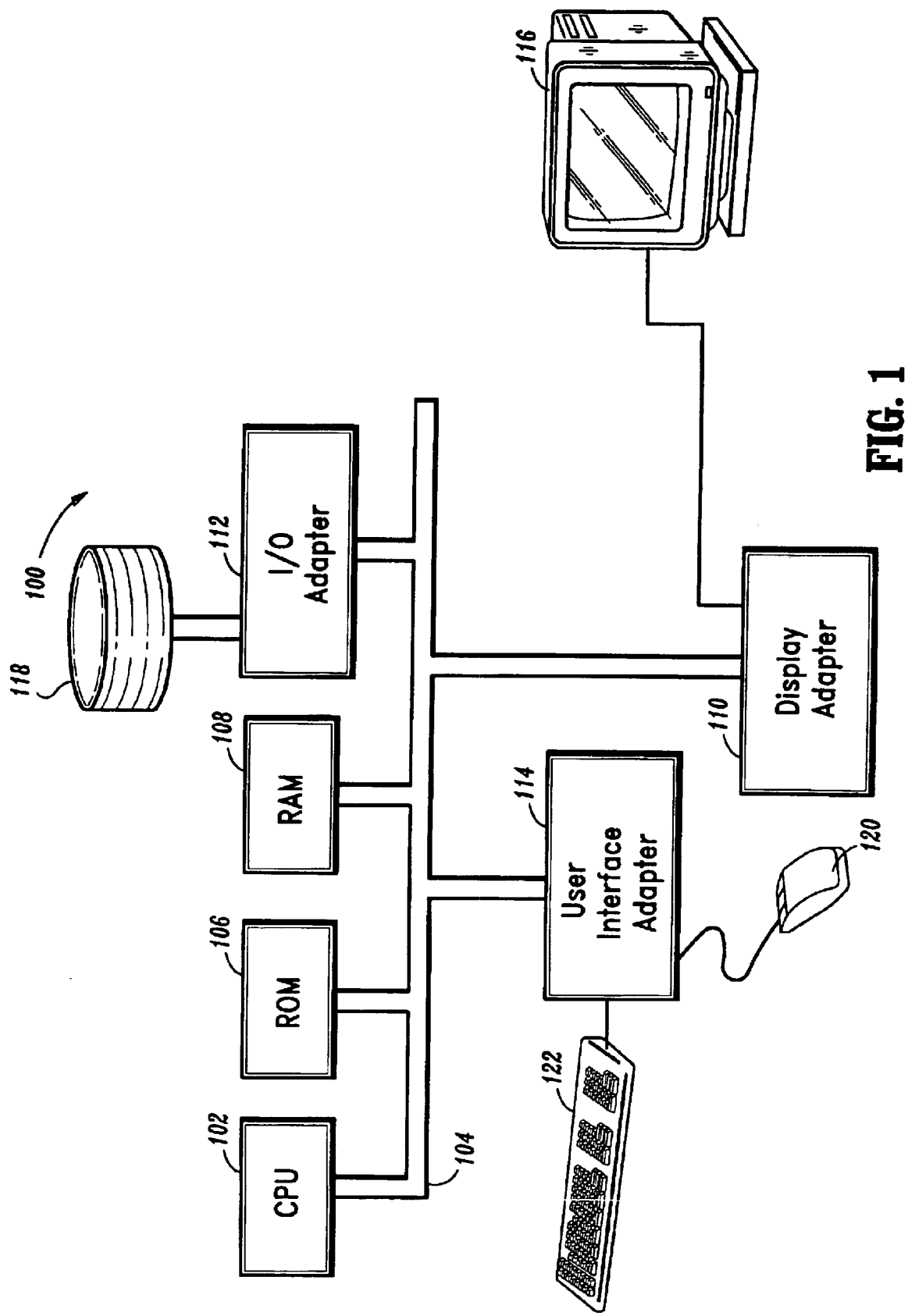
FIG. 1 is a block diagram of a computer processing system 100 to which the present invention may be applied according to an illustrative embodiment thereof.

FIG. 1 is a block diagram of a computer processing system 100 to which the present invention may be applied according to an illustrative embodiment thereof. The computer processing system 100 includes at least one processor (CPU) 102 operatively coupled to other components via a system bus 104. A read only memory (ROM) 106, a random access memory (RAM) 108, a display adapter 110, an I/O adapter 112, and a user interface adapter 114 are operatively coupled to the system bus 104.

A display device 116 is operatively coupled to the system bus 104 by the display adapter 110. A disk storage device (e.g., a magnetic or optical disk storage device) 118 is operatively coupled to the system bus 104 by the I/O adapter 112.

A mouse 120 and keyboard 122 are operatively coupled to the system bus 104 by the user interface adapter 114. The mouse 120 and keyboard 122 may be used to input/output information to/from the computer processing system 100.

A brief description of the present invention will now be given, following by more detailed descriptions of various illustrative embodiments of the present invention provided with respect to FIGS. 2–4.

Light is directed to a target and the reflected beam is measured by a detector. The optical measurements are taken from a patterned area of a wafer of a semiconductor device. The patterned area includes features of interest for which information corresponding thereto is desired. For example, the dimensions of a trench which are filled with polysilicon may be measured using the present invention.

The optical measurements can be ellipsometric, scatterometric, reflectometric, polarimetric, or any combination of these or similar techniques, as are known to those of ordinary skill in the related art. Changes in grating composition and features affect the optically measured characteristics. Analysis of these characteristics is used to determine information about the target (e.g., sizes and compositions of features of interest).

Figure 2:
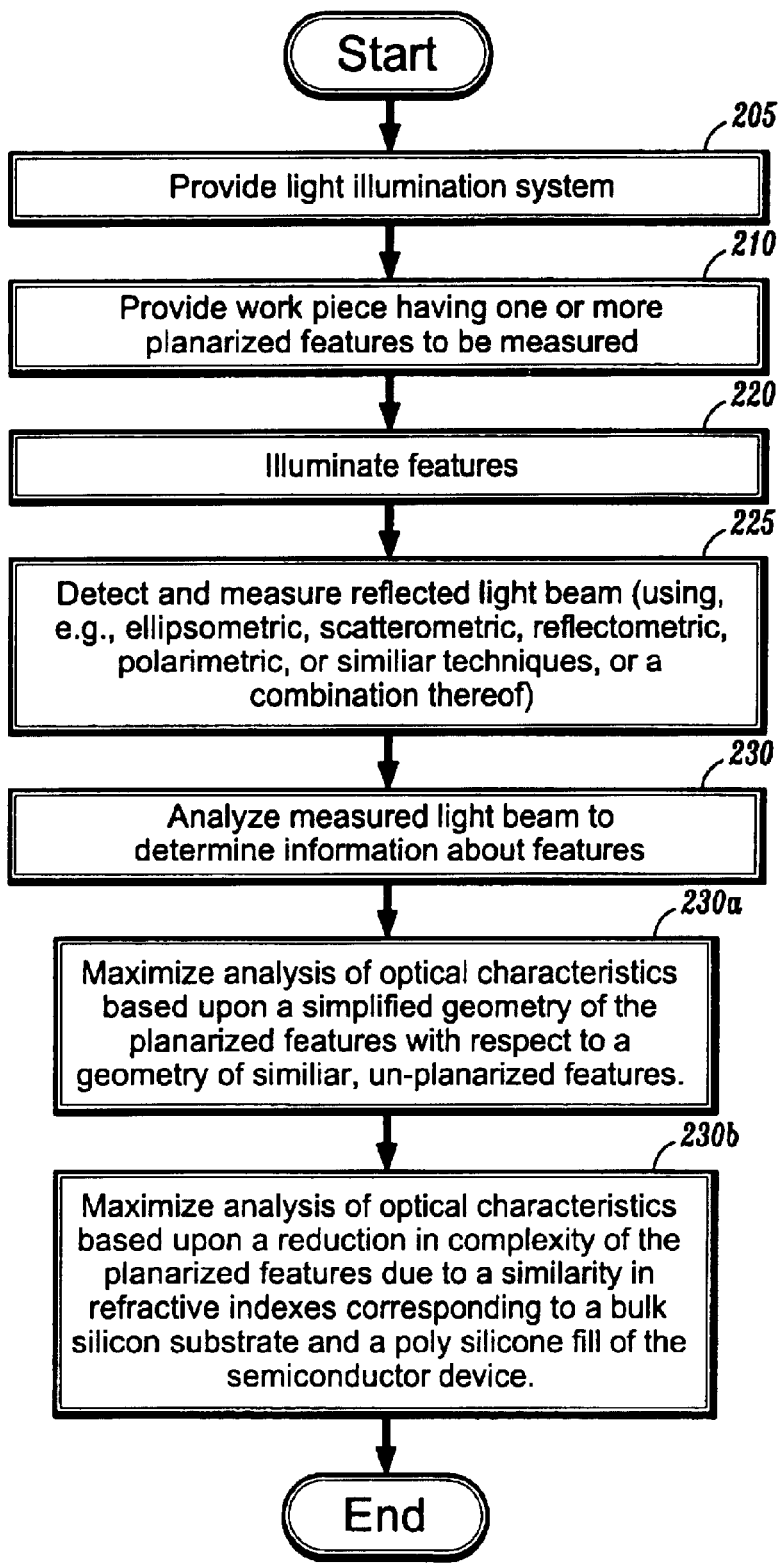
FIG. 2 is a flow diagram illustrating a method for optical measurement of planarized features, according to an illustrative embodiment of the present invention.

FIG. 2 is a flow diagram illustrating a method for optical measurement of planarized features, according to an illustrative embodiment of the present invention.

In block 205, a light illumination system is provided. It is to be appreciated that the present invention may be employed with any type of light illumination system, and thus, the present invention is not limited to any particular type of light illumination system. These systems are modified as described herein to provide the feature measurement capabilities as described in accordance with the present invention.

In block 210, a work piece is provided, such as a semiconductor device. The work piece includes one or more planarized features to be measured.

The illumination system provided in step 205 includes an exposure system and a detection system. In block 220, the planarized features on the work piece are illuminated by the exposure system.

In block 225, the detection system is employed to detect and measure the light beam reflected by the planarized features on the work piece. Block 225 may be performed using, for example, ellipsometric, scatterometric, reflectometric, polarimetric, or any combination of these or similar techniques, as are known to those of ordinary skill in the related art.

In block 230, the measured light beam is analyzed (optical characteristics) to determine information about the planarized features. Such information may include, for example, size, grating composition, and so forth. However, the main interest for the present invention is the critical dimensions of poly filled features. A number of methods can be used to extract the critical dimensions, one involves building a database on prior measurements and then comparing it with the spectra of the data under analysis. Another may be real time calculation of the critical dimensions from spectra using appropriate algorithms. The invention is independent on the choice of the analysis method.

It is to be appreciated that block 230 preferably includes blocks 230a and 230b. In block 230a, the analyzing step (block 230) is performed so as to maximize an analysis of the optical characteristics based upon a simplified geometry of the planarized features with respect to a geometry of similar, un-planarized features. In block 230b, the analyzing step (block 230) is performed so as to maximize an analysis of the optical characteristics based upon a reduction in complexity of the planarized features due to a similarity in refractive indexes corresponding to a bulk silicon substrate and a poly silicon fill of the semiconductor device.

Figure 3:
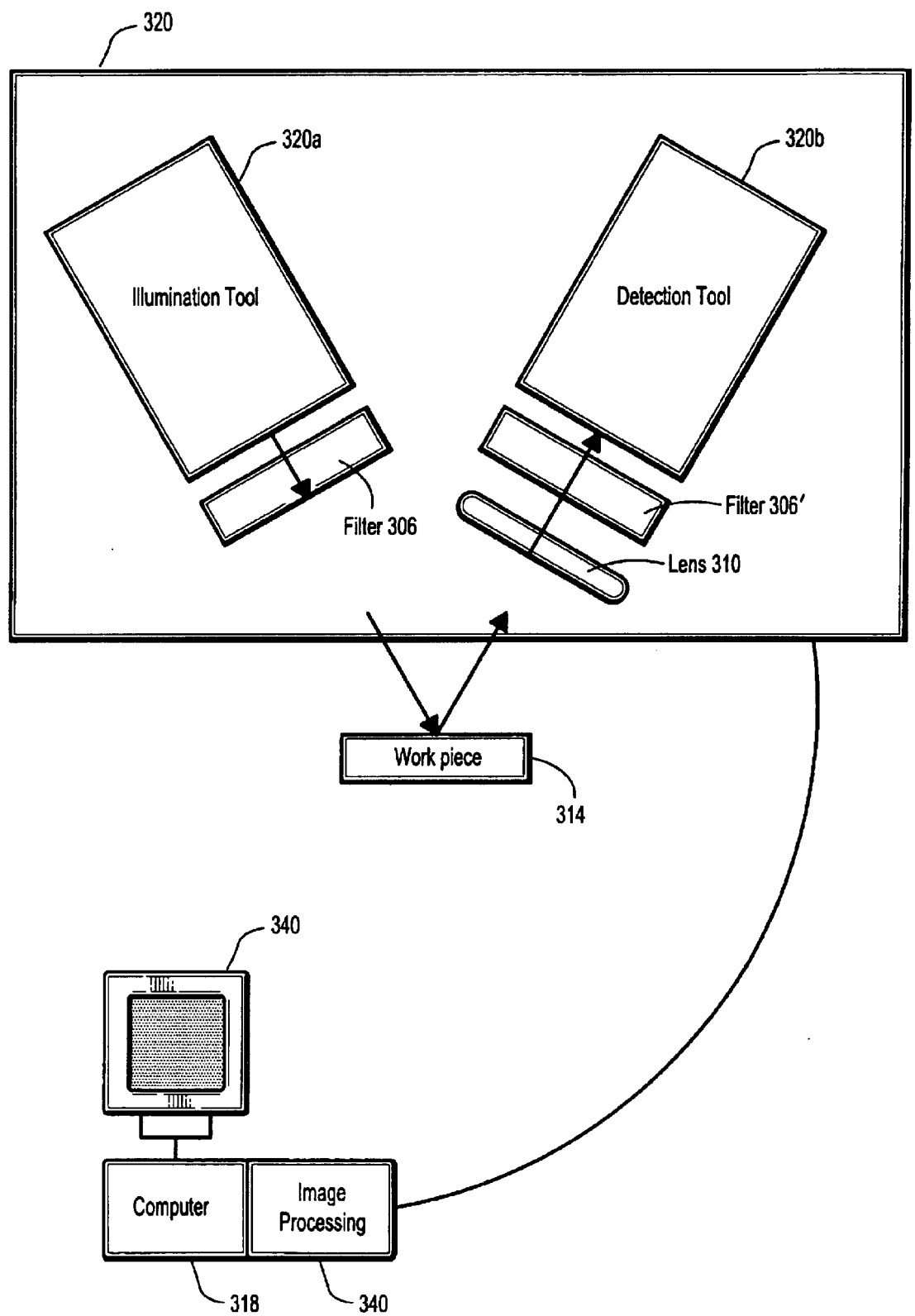
FIG. 3 is a block diagram illustrating a system 300 for optical measurement of planarized features, according to an illustrative embodiment of the present invention.

FIG. 3 is a block diagram illustrating a system 300 for optical measurement of planarized features, according to an illustrative embodiment of the present invention.

The system 300 includes an illumination system 320. The illumination system 320 includes an exposure or illumination tool (hereinafter "illumination tool") 320a for providing light to illuminate a work piece 314. The illumination tool 320 may be, for example, a broadband illumination tool, a single wavelength illumination tool, or any other type of illumination or exposure tool.

Work piece 314 may include a semiconductor wafer having planarized features to be measured.

Illumination tool 320a propagates light onto the planarized features of the work piece 314. In preferred embodiments, light from illumination tool 320a passes through a filter module 306 either before hitting the work piece 314 or after being reflected from the work piece 314. An additional filter module 306' may be included at a detection tool 320b (included in illumination system 320) to filter light, which has been reflected from the work piece 314. The additional filter module 306' may be included in addition to or instead of the filter module 306. Filter modules may both be included to increase the number of available filters or to provide additional filtering. Given the teachings of the present invention provided herein, one of ordinary skill in the related art will contemplate these and various other configurations and alternations of the elements of system 300, while maintaining the spirit and scope of the present invention.

Detection tool 320b includes sensors for the detection of light reflected back from the planarized features on the work piece 314. Illumination and detection tools 320a and 320b, respectively, may be the type commonly provided on illumination systems. Thus, it is to be appreciated that, for the sake of brevity, some components typically found in an illumination system are not shown and described but may nonetheless be included in illumination system 320, while maintaining the spirit and scope of the present invention. Such components may include, for example, an adjustable or variable aperture for the detection tool 320b.

Lens 310 collects reflected light from the planarized features on the work piece 314. After collecting light reflected from the planarized features on the work piece 314, a computer processing system 318, having an image processing program 340 stored thereon, is preferably employed to analyze the measured light. The computer processing system 318 may include a display 340 for displaying the results of the analysis.

Figure 4:
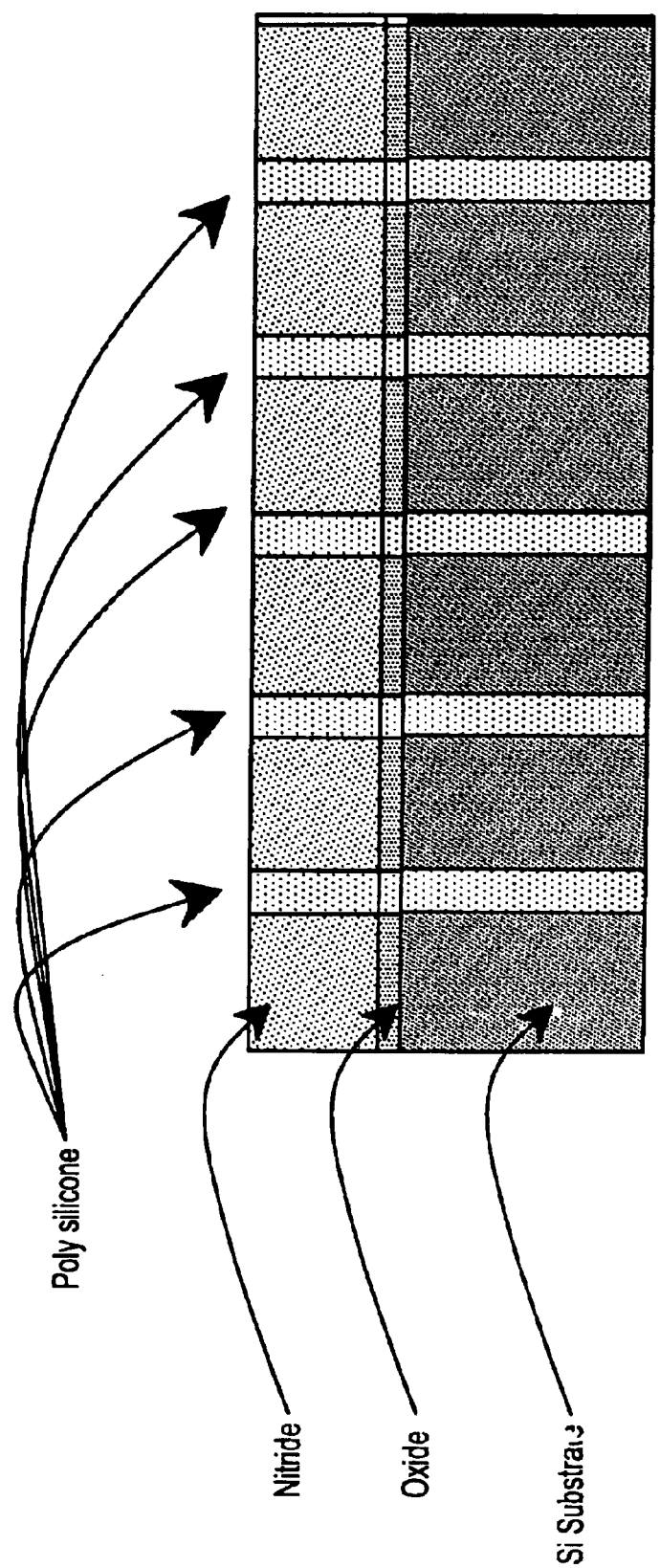
FIG. 4 is a block diagram illustrating a typical work piece to which the present invention may be applied, according to an illustrative embodiment thereof.

FIG. 4 is a block diagram illustrating a typical work piece to which the present invention may be applied, according to an illustrative embodiment thereof. The work piece illustrated in FIG. 4 is poly-filled using planarized DRAM techniques, and includes a nitride layer, an oxide layer, and an silicon (SI) substrate.

Simulations corresponding to the present invention have been performed using Rigorous Coupled Wave Analysis. On every incoming wafer, for example, trench openings are measured and the data stored at the tool level. These simulations show that the reflected and diffracted orders are sensitive to changes in the critical dimensions.

Although the illustrative embodiments have been described herein with reference to the accompanying drawings, it is to be understood that the present invention is not limited to those precise embodiments, and that various other changes and modifications may be affected therein by one of ordinary skill in the related art without departing from the scope or spirit of the invention. All such changes and modifications are intended to be included within the scope of the invention as defined by the appended claims.

What is claimed is:

1. A method for measuring planarized features on a wafer of a semiconductor device, comprising the steps of:

illuminating the planarized features on the wafer;

detecting a reflected light beam with respect to the planarized features; and analyzing optical characteristics of the reflected light beam to determine information corresponding to the planarized features, wherein said analyzing step maximizes an analysis of the optical characteristics based upon a reduction in complexity of the planarized features due to a similarity in refractive indexes corresponding to a bulk silicon substrate and a poly silicon fill of the semiconductor device.

2. The method of claim 1, wherein the information comprises sizes of the planarized features.

3. The method of claim 1, wherein the information comprises grating compositions of the planarized features.

4. The method of claim 1, wherein said detecting step is performed using an ellipsometric technique.

5. The method of claim 1, wherein said detecting step is performed using a scatterometric technique.

6. The method of claim 1, wherein said detecting step is performed using a reflectometric technique.

7. The method of claim 1, wherein said detecting step is performed using a polarimetric technique.

8. The method of claim 1, wherein said detecting step is performed using at least one of an ellipsometric, a scatterometric, a reflectometric, and a polarimetric technique.

9. The method of claim 1, wherein said analyzing step maximizes an analysis of the optical characteristics based upon a simplified geometry of the planarized features with respect to a geometry of similar, un-planarized features.

10. A system for measuring planarized features on a wafer of a semiconductor device, comprising:

an illumination tool for illuminating the planarized features on the wafer;

a detection tool for detecting a reflected light beam with respect to the planarized features; and an analysis tool for analyzing optical characteristics of the reflected light beam to determine information corresponding to the planarized features, wherein said analysis tool maximizes an analysis of the optical characteristics based upon a reduction in complexity of the planarized features due to a similarity in refractive indexes corresponding to a bulk silicon substrate and a poly silicon fill of the semiconductor device.

11. The system of claim 10, wherein the information comprises sizes of the planarized features.

12. The system of claim 10, wherein the information comprises grating compositions of the planarized features.

13. The system of claim 10, wherein said detection tool employs an ellipsometric technique to detect the reflected light.

14. The system of claim 10, wherein said detection tool employs a scatterometric technique to detect the reflected light.

15. The system of claim 10, wherein said detection tool employs a reflectometric technique to detect the reflected light.

16. The system of claim 10, wherein said detection tool employs a polarimetric technique to detect the reflected light.

17. The system of claim 10, wherein said detection tool employs at least one of an ellipsometric, a scatterometric, a reflectometric, and a polarimetric technique to detect the reflected light.

18. The system of claim 10, wherein said analysis tool maximizes an analysis of the optical characteristics based upon a simplified geometry of the planarized features with respect to a geometry of similar, un-planarized features.

19. A method for measuring planarized features on a wafer of a semiconductor device, comprising the steps of:
 illuminating the planarized features on the wafer;
 detecting a reflected light beam with respect to the planarized features; and
 analyzing optical characteristics of the reflected light beam to determine information corresponding to the planarized features, wherein said analyzing step comprises the step of:
  maximizing an analysis of the optical characteristics based upon a simplified geometry of the planarized features with respect to a geometry of similar, un-planarized features.

* * * * *